United States Patent [19]

Beard et al.

[11] Patent Number: 5,672,710

[45] Date of Patent: Sep. 30, 1997

[54] SULFIDES, SULFOXIDES AND SULFONES DISUBSTITUTED WITH A TETRAHYDRONAPHTHALENYL, CHROMANYL, THIOCHROMANYL OR TETRAHYDROQUINOLINYL AND SUBSTITUTED PHENYL OR HETEROARYL GROUP, HAVING RETINOID-LIKE BIOLOGICAL ACTIVITY

[75] Inventors: Richard L. Beard, Newport Beach; Diana F. Colon, Irvine; Roshantha A. Chandraratna, Mission Viejo, all of Calif.

[73] Assignee: Allergan, Waco, Tex.

[21] Appl. No.: 552,965

[22] Filed: Nov. 3, 1995

[51] Int. Cl.⁶ .................................................. C07D 277/24
[52] U.S. Cl. ........................ 548/188; 544/239; 544/318; 544/406; 548/230; 548/322.5; 548/369.7
[58] Field of Search ............................... 544/239, 318, 544/406; 546/298; 548/188, 230, 322.5, 369.7; 549/64, 479; 560/17

[56] References Cited

U.S. PATENT DOCUMENTS

| | | |
|---|---|---|
| 4,096,341 | 6/1978 | Frazer . |
| 4,326,055 | 4/1982 | Loeliger . |
| 4,391,731 | 7/1983 | Boller et al. ............... 252/299.62 |
| 4,695,649 | 9/1987 | Magami et al. . |
| 4,723,028 | 2/1988 | Shudo . |
| 4,739,098 | 4/1988 | Chandraratna . |
| 4,740,519 | 4/1988 | Shroot et al. . |
| 4,810,804 | 3/1989 | Chandraratna . |
| 4,826,969 | 5/1989 | Maignan et al. . |
| 4,826,984 | 5/1989 | Berlin et al. ............... 546/134 |
| 4,855,320 | 8/1989 | Chatterjee et al. . |
| 4,895,868 | 1/1990 | Chandraratna . |
| 4,927,947 | 5/1990 | Chandraratna ............... 549/484 |
| 4,980,369 | 12/1990 | Chandraratna . |
| 4,992,468 | 2/1991 | Chandraratna . |
| 5,006,550 | 4/1991 | Chandraratna . |
| 5,013,744 | 5/1991 | Chandraratna . |
| 5,015,658 | 5/1991 | Chandraratna . |
| 5,023,341 | 6/1991 | Chandraratna . |
| 5,037,825 | 8/1991 | Klaus et al. ............... 514/233.8 |
| 5,045,551 | 9/1991 | Chandraratna . |
| 5,053,523 | 10/1991 | Chandraratna . |
| 5,068,252 | 11/1991 | Chandraratna . |
| 5,089,509 | 2/1992 | Chandraratna . |
| 5,130,335 | 7/1992 | Chandraratna . |
| 5,134,159 | 7/1992 | Chandraratna . |

(List continued on next page.)

FOREIGN PATENT DOCUMENTS

| | | |
|---|---|---|
| A-16512/95 | 11/1995 | Australia . |
| 170105A | of 0000 | European Pat. Off. . |
| 0098591 | 1/1984 | European Pat. Off. ...... C07D 333/54 |
| 0130795 | 1/1985 | European Pat. Off. ...... C07D 311/58 |
| 0176032 | 4/1986 | European Pat. Off. ....... C07C 65/38 |
| 0176033 | 4/1986 | European Pat. Off. ...... C07D 261/18 |
| 176034A | 4/1986 | European Pat. Off. ........ C07C 63/66 |
| 0253302 | 1/1988 | European Pat. Off. ...... C07D 213/16 |
| 0272921 | 6/1988 | European Pat. Off. ...... C07D 213/80 |
| 0284288 | 9/1988 | European Pat. Off. ...... C07D 401/04 |
| 0303915 | 2/1989 | European Pat. Off. ...... A61K 31/255 |
| 0315071 | 5/1989 | European Pat. Off. ........ C07C 63/66 |
| 0350846 | 7/1989 | European Pat. Off. ...... C07D 311/58 |
| 0661259 | 5/1995 | European Pat. Off. ...... C07C 233/81 |
| 2719043 | 10/1995 | France . |
| 3316932 | 11/1983 | Germany ...................... C07C 63/66 |
| 3524199 | 1/1986 | Germany ...................... C07C 63/66 |
| 3602473 | 7/1987 | Germany ...................... C07C 43/215 |
| 3708060 | 9/1987 | Germany ...................... C07D 311/04 |
| 3715955 | 11/1987 | Germany ...................... C07C 15/58 |
| 2190378 | 11/1987 | United Kingdom ........... C07C 39/21 |
| 8500806 | 2/1985 | WIPO ........................ A61K 31/00 |
| 8504652 | 10/1985 | WIPO ........................ A61K 31/19 |
| WO9116051 | 10/1991 | WIPO ........................ A61K 31/44 |
| WO9206948 | 4/1992 | WIPO ........................ C07C 69/86 |

OTHER PUBLICATIONS

A General Synthesis of Terminal and Internal Arylalkynes by the Palladium–Catalyzed Reaction of Alkynylzinc Reagents with Aryl Halides by Anthony O. King and Ei–ichi Negishi, J. Org. Chem. 43 No. 2, 1978 p. 358.

Conversion of Methyl Ketones into Terminal Acetylenes and (E)–Tri–substituted Olefins of Terpenoid Origin by Ei–ichi, Anthony O. King, and William L. Klima, J. Org. Chem. 45 No. 12, 1980 p. 2526.

Sporn et. al. in J. Amer. Acad. Derm. 15:756–764 1986.

A Convenient Synthesis of Ethynylarenes and Diethynylarenes by S. Takahashi, Y. Kuroyama, K. Sonogashira, N. Hagihara, Synthesis 1980 pp. 627–630.

Shudo et al. in Chem. Phar. Bull. 33:404–407 1985.

Kagechika et. al. in J. Med. Chem. 31:2182–2192 1988.

Chemistry and Biology of Synthetic Retinoids by Marcia I. Dawson and William H. Okamura, published by CRC Press Inc., 1990, pp. 334–335, 354.

Synthesis of 2.2'–Diacyl–1,1'–biaryls. Regiocontrolled Protection of . . . by Mervic, et al, J. Org. Chem., No. 45, pp. 4720–4725, 1980.

A Dopamine Receptor Model and Its Application in the Design of a New Class of Rigid Pyrrolo[2,3–g]isoquinoline Antipsychotics, Gary L. Olson, et al. *American Chemical Society*, 1981, Vo. 24, No. 9, pp. 1026–1031.

(List continued on next page.)

Primary Examiner—Patricia L. Morris
Assistant Examiner—Garth M. Dahlen
Attorney, Agent, or Firm—Gabor L. Szekeres; Robert J. Baran; Martin A. Voet

[57] ABSTRACT

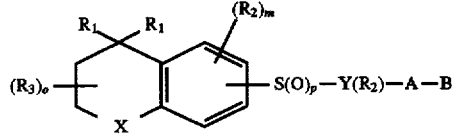

wherein the symbols have the meaning described in the specification, are selective agonists of RXR retinoid receptors.

10 Claims, No Drawings

U.S. PATENT DOCUMENTS

| | | | |
|---|---|---|---|
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |

OTHER PUBLICATIONS 6.2.3 Conformational Restriction, Williams, et al., *Drug Discovery and Development*, 1987 The Humana Press, pp. 54–55.

V. Retinoid Structure–Biological Activity Relationship, Chemistry and Biology of Synthetic Retinoids, pp. 324–356, 1990.

Davis et al. *J. Organomettalic Chem* 387 (199) 381–390.

Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13–cis retinoic acid and testosterone, John Ridden, et al., *Journal of Cell Science*, Vo. 95, pp. 125–136.

Characterization of Human Sebaceous Cells In Vitro, Thomas I. Doran, et al., *The Journal of Investigative Dermatology*, vol. 96, No. 3, Mar. 1991.

Synthesis and Evaluation of Stilbene and Dihydrostilbene Derivatives as Potential Anticancer Agents That Inhibit Tubulin Polymerization by Cushman, Mark et. al. *J.Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters*, vol. 1, No. 4, pp. 211–214, 1991.

Di–and Tri–methozystyryl Derivatives of Heterocyclic Nitrogen Compounds by Bahner, C.T. et al. Arzneim–Forsch./Drug Res, 31 (I), Nr. 3 (1981).

Retinobenzoic acids. 3. Structure–Activity Relationships of retinoidal Azobenzene–4–carboxylic acids and Stilbene–4–carboxlic acids by H. Kagechika et al., *Journal of Medicinal Chemistry*, 1989, 32, pp. 1098–1108.

SULFIDES, SULFOXIDES AND SULFONES DISUBSTITUTED WITH A TETRAHYDRONAPHTHALENYL, CHROMANYL, THIOCHROMANYL OR TETRAHYDROQUINOLINYL AND SUBSTITUTED PHENYL OR HETEROARYL GROUP, HAVING RETINOID-LIKE BIOLOGICAL ACTIVITY

FIELD OF THE INVENTION

The present invention relates to novel compounds having retinoid-like biological activity. More specifically, the present invention relates to sulfide, sulfoxide and sulfone compounds disubstituted with a tetrahydronapthalenyl, chromanyl, thiochromanyl or tetrahydroquinolinyl and substituted phenyl or heteroaryl group having retinoid-like biological activity.

BACKGROUND ART

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and in the treatment and prevention of diabetes and obesity and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis. U.S. Pat. Nos. 4,740,519 (Shroot et al.), 4,826,969 (Maignan et al.), 4,326,055 (Loeliger et al.), 5,130,335 (Chandraratna et al.), 5,037,825 (Klaus et al.), 5,231,113 (Chandraratna et al.), 5,324,840 (Chandraratna), 5,344,959 (Chandraratna), 5,130,335 (Chandraratna et al.), Published European Patent Application Nos. 0 176 034 A (Wuest et al.), 0 350 846 A (Klaus et al. ), 0 176 032 A (Frickel et al.), 0 176 033 A (Frickel et al.), 0 253 302 A (Klaus et al.), 0 303 915 A (Bryce et al. ), UK Patent Application GB 2190378 A (Klaus et al.), German Patent Application Nos. DE 3715955 A1 (Klaus et al.), DE 3602473 A1 (Wuest et al., and the articles J. Amer. Acad. Derm. 15:756–764 (1986) (Sporn et al.), Chem. Pharm. Bull. 33: 404–407 (1985) (Shudo et al.), J. Med Chem. 1988 31, 2182–2192 (Kagechika et al.), Chemistry and Biology of Synthetic Retinoids CRC Press Inc. 1990 p 334–335, 54 (Dawson et al.), describe or relate to compounds which include a tetrahydronaphthyl moiety and have retinoid-like or related biological activity. U.S. Pat. No. 4,391,731 (Boller et al.) describes tetrahydronaphthalene derivatives which are useful in liquid crystal compositions.

U.S. Pat. Nos. 4,980,369, 5,006,550, 5,015,658, 5,045,551, 5,089,509, 5,134,159, 5,162,546, 5,234,926, 5,248,777, 5,264,578, 5,272,156, 5,278,318, 5,324,744, 5,346,895, 5,346,915, 5,348,972, 5,348,975, 5,380,877, 5,399,561, 5,407,937, (assigned to the same assignee as the present application) and patents and publications cited therein, describe or relate to chroman, thiochroman and 1,2,3,4-tetrahydroquinoline derivatives which have retinoid-like biological activity. Still further, several co-pending applications and recently issued patents which are assigned to the assignee of the present application, are directed to further compounds having retinoid-like activity.

It is now general knowledge in the art that two main types of retinoid receptors exist in mammals (and other organisms). The two main types or families of receptors respectively designated the RARs and RXRs. Within each type there are subtypes; in the RAR family the subtypes are designated RAR$_\alpha$, RAR$_\beta$ and RAR$_\Gamma$, in RXR the subtypes are: RXR$_\alpha$, RXB$_\beta$ and RXR$_\Gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

The present invention provides further compounds having retinoid-like biological activity and specifically compounds which are specific or highly selective agonists of RXR retinoid receptors in preferance over RAR retinoid receptors.

SUMMARY OF THE INVENTION

The present invention covers compounds of Formula

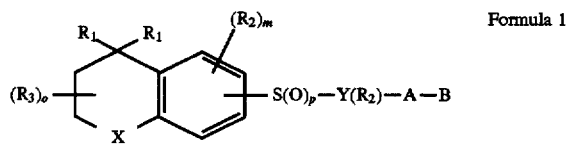

Formula 1 wherein X is S, O, NR' where R' is H or alkyl of 1 to 6 carbons, or

X is $[C(R_1)_2]_n$ where n is an integer between 0 and 2;

$R_1$ is independently H or alkyl of 1 to 6 carbons;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–4;

p is an integer having the value of 0–2;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, $COOR_8$, $CONR_9R_{10}$, $—CH_2OH$, $CH_2OR_{11}$, $CH_2OCOR_{11}$, CHO, $CH(OR_{12})_2$, $CHOR_{13}O$, $—COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or (trimethylsilyl) alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising a compound of Formula 1 in admixture with a pharmaceutically acceptable excipient.

In another aspect, this invention relates to processes for making a compound of Formula 1 which processes comprise reacting a compound of Formula 2, or a suitable salt such as a sodium salt of a compound of Formula 2 with a compound of Formula 3 (where $X_1$ is halogen and Y, $R_2$, A and B are defined as in connection with Formula 1) in the presence of base and preferably in the presence of a catalyst, and also to the processes of oxidizing a sulfide compound of Formula 1 (p=0) to the corresponding sulfoxide or sulfone compound of Formula 1 (p=1 or p=2).

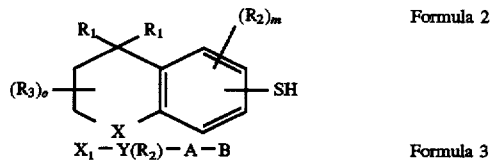

Formula 2

Formula 3

Still further, the present invention relates to such reactions performed on the compounds of Formula 1 which cause transformations of the B group while the reaction product still remains within the scope of Formula 1.

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula I is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and disubstituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered. Pharmaceutically acceptable salts may be derived from organic or inorganic bases. The salt may be a mono or polyvalent ion. Of particular interest are the inorganic ions, sodium, potassium, calcium, and magnesium. Organic salts may by be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference to the symbol Y in Formula 1, the preferred compounds of the invention are those where Y is phenyl, pyridyl, 2-thiazolyl, thienyl, or furyl, even more preferably, phenyl, pyridyl and 2-thiazolyl. As far as substitutions on the Y (phenyl) and Y (pyridyl) groups are concerned, compounds are preferred where the phenyl group is 1,4 (para) substituted by the S=(O)$_p$ and A–B groups, and where the pyridine ring is 2,5 substituted by the S=(O)$_p$ and A–B groups. (Substitution in the 2,5 positions in the "pyridine" nomenclature corresponds to substitution in the 6-position in the "nicotinic acid" nomenclature.) When the Y group is thiazole it is preferably substituted in the 2 position by the S=(O)$_p$ group and in the 5 position by the A–B group. In the preferred compounds of the invention there is no optional R$_2$ substituent on the Y group.

With reference to the symbol X in Formula 1, compounds are preferred in accordance with the invention where X is [C(R$_1$)$_2$]$_n$ and n is 1, and also where X is O or S (chroman and thiochroman derivatives). Even more preferred are compounds where X is [C(R$_1$)$_2$]$_n$ and n is 1 (tetrahydronaphthalene derivatives). The presently preferred compounds of the invention are sulfides, and therefore p of Formula 1 is preferably zero.

The R$_1$ groups are preferably H or CH$_3$, and the preferred R$_2$ group on the aromatic portion of the condensed ring moiety is H, lower alkyl, F or CF$_3$, even more preferably H or CH$_3$. The R$_3$ group is preferably hydrogen; in other words the non-aromatic portion of the condensed ring moiety is preferably substituted only by the R$_1$ groups.

The A–B group of the preferred compounds is (CH$_2$)$_n$—COOH or (CH$_2$)$_n$—COOR$_8$, where n and R$_8$ are defined as above. Even more preferably n is zero and R$_8$ is lower alkyl, or n is zero and B is COOH or a pharmaceutically acceptable salt thereof.

The presently most preferred compounds of the invention are shown in Table 1 with reference to Formula 4 and Formula 5.

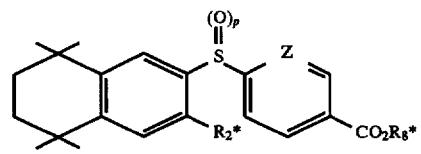

Formula 4

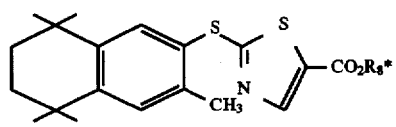

Formula 5

TABLE 1

| Compound # | Formula | p | Z | R$_2$* | R$_8$* |
|---|---|---|---|---|---|
| 1 | 4 | 0 | CH | H | Et |
| 2 | 4 | 0 | CH | H | H |
| 3 | 4 | 1 | CH | H | Et |
| 4 | 4 | 2 | CH | H | Et |
| 5 | 4 | 2 | CH | H | H |
| 6 | 4 | 0 | CH | CH$_3$ | Et |
| 7 | 4 | 0 | CH | CH$_3$ | H |
| 8 | 4 | 1 | CH | CH$_3$ | Et |
| 9 | 4 | 1 | CH | CH$_3$ | H |
| 10 | 4 | 2 | CH | CH$_3$ | Et |
| 11 | 4 | 2 | CH | CH$_3$ | H |
| 12 | 4 | 0 | N | CH$_3$ | Et |
| 13 | 4 | 0 | N | CH$_3$ | H |

TABLE 1-continued

| Compound # | Formula | p | Z | $R_2$* | $R_a$* |
|---|---|---|---|---|---|
| 14 | 5 | 0 | — | — | Et |
| 15 | 5 | 0 | — | — | H |

Modes of Administration

The compounds of this invention may be administered systemically or topically, depending on such considerations as the condition to be treated, need for site-specific treatment, quantity of drug to be administered, and numerous other considerations. In the treatment of dermatoses, it will generally be preferred to administer the drug topically, though in certain cases such as treatment of severe cystic ache or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many disease for which these compounds are useful.

Assay of Retinoid-like Biological Activity The retinoid-like activity of the compounds of the invention can be confirmed in assays wherein ability of the compound to modulate processes mediated by retinoid receptors, and ability of the compounds to bind to retinoid receptors is measured. As it is noted in the introductory section of this application for patent two main types of retinoic acid receptors (RAR and RXR) exist in mammals (and other organisms). Within each type there are sub-types ($RAR_\alpha$, $RAR_\beta$, $RAR_\gamma$, $RXR_\alpha$, $RXR_\beta$ and $RXR_\gamma$) the distribution of which is not uniform in the various tissues and organs of mammalian organisms. Moreover, specific or selective agonist-like activity on RXR receptors, in preference over RAR receptors tends to result in certain beneficial retinoid-like properties while avoiding certain undesirable side effects. Similarly, selective agonist like activity of only one or two retinoid receptor subtypes within one retinoid receptor family can also give rise to beneficial pharmacological properties because of the varying distribution of the sub-types in the several mammalian tissues or organs. For the above-summarized reasons, agonist-like activity in any or all of the retinoid receptors, as well as specific or selective activity in the RXR receptor family, or selective or specific activity in any one of the receptor subtypes, are all considered desirable pharmacological properties.

In light of the foregoing the prior art has developed assay procedures for testing the agonist like activity of compounds in the $RAR_\alpha$, $RAR_\beta$, $RAR_\gamma$, $RXR_\alpha$, $RXR_\beta$ $_{and\ RXR\gamma}$receptor subtypes. For example, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 11 2 is described in detail in U.S. Pat. No. 5,455,265. The specification of U.S. Pat. No. 5,455,265 is expressly incorporated herein by reference.

A holoreceptor transactivation assay and a ligand binding assay which measure the ability of the compounds of the invention to bind to the several retinoid receptor subtypes, respectively, are described in published PCT Application No. WO W093/11755 (particularly on pages 30–33 and 37–41) published on Jun. 24, 1993, the specification of which is also incorporated herein by reference. A description of the holoreceptor transactivation assay is also provided below.

HOLORECEPTOR TRANSACTIVATION ASSAY

CV1 cells (5,000 cells/well) were transfected with an RAR reporter plasmid MTV-TREp-LUC (50 ng) along with one of the PAR expression vectors (10 ng) in an automated 96-well format by the calcium phosphate procedure of Heyman et al. Cell 68, 397–406. (8). For $RXR_\alpha$and $RXR_\gamma$transactivation assays, an RXR-responsive reporter plasmid CRBPII-tk-LUC (50 ng) along with the appropriate RXRexpression vectors (10 ng) was used substantially as described by Heyman et al. above, and Allegretto et al. J. Biol. Chem. 268, 26625–26633. For $RXR_\beta$ transactivation assays, an RXR-responsive reporter plasmid CPRE-tk-LUC (50 mg) along with $RXR_\beta$ expression vector (10 mg) was used as described in above. These reporters contain DRI elements from human CRBPII and certain DRI elements from promoter, respectively. (see Mangelsdorf et al. The Retinoids: Biology, Chemistry and Medicine, pp 319–349, Raven Press Ltd., New York and Heyman et al., cited above) (1, 8). A β-galactosidase (50 ng) expression vector was used as an internal control in the transfections to normalize for variations in transfection efficiency. The cells were transfected in triplicate for 6 hours, followed by incubation with retinoids for 36 hours, and the extracts were assayed for luciferase and β-galactosidase activities. The detailed experimental procedure for holoreceptor transactivations has been described in Heyman et al. above, and Allegretto et al. cited above. The results obtained in this assay in connection with examplary compounds in accordance with the present invention are expressed in $EC_{50}$ numbers, as they are also in the chimeric receptor transactivation assay. The Heyman et al. Cell 68, 397–406, Allegretto et al. J. Biol. Chem. 268, 26625–26633, and Mangelsdorf et al. The Retinoids: Biology, Chemistry and Medicine, pp 319–349, Raven Press Ltd., New York, are expressly incorporated herein by reference. The results of ligand binding assay are expressed in $K_d$ numbers. (See Cheng et al. Biochemical Pharmacology Vol. 22 pp 3099–3108, expressly incorporated herein by reference.)

Table 2 below shows the results of the holoreceptor transactivation assay and Table 3 discloses the efficacy (in percentage) in this assay of the test compound relative to all trans retinoic acid, for certain exemplary compounds of the invention. Table 4 shows the results of the ligand binding assay for certain exemplary compounds of the invention.

TABLE 2

Holoreceptor Transactivation Assay $EC_{50}$ (nanomolar)

| Compound # | RARα | RARβ | RARΓ | RXRα | RXRβ | RXRΓ |
|---|---|---|---|---|---|---|
| 2 | 0.00 | 570 | 340 | 770 | 1600 | 1600 |
| 5 | 0.00 | 0.00 | 0.00 | 3000 | 0.00 | 2600 |
| 7 | 0.00 | 0.00 | 0.00 | 280 | 320 | 230 |
| 9 | 0.00 | 0.00 | 0.00 | 0.00 | 3000 | 1600 |
| 11 | 0.00 | 0.00 | 0.00 | 2800 | 2600 | 2600 |
| 13 | 0.00 | 0.00 | 0.00 | 54 | 57 | 42 |
| 15 | 0.00 | 0.00 | 0.00 | 2300 | 1300 | 1900 |

0.0 in Table 2 indicates that the compound is less than 20% as active (efficacious) in this assay than all trans retinoic acid.

TABLE 3

Transactivation Assay Efficacy (% of RA activity)

| Compound # | RARα | RARβ | RARΓ | RXRα | RXRβ | RXRΓ |
|---|---|---|---|---|---|---|
| 2 | 3 | 66 | 37 | 51 | 80 | 75 |
| 5 | 10 | 4 | 0 | 32 | 11 | 26 |
| 7 | 3 | 4 | 11 | 81 | 114 | 67 |
| 9 | 5 | 4 | 3 | 17 | 29 | 28 |
| 11 | 2 | 6 | 0 | 55 | 52 | 45 |
| 13 | 1 | 4 | 0 | 91 | 100 | 85 |
| 15 | 1 | 0 | 7 | 85 | 117 | 70 |

TABLE 4

Ligand Binding Assay $K_d$ (nanomolar)

| Compound # | RARα | RARβ | RARΓ | RXRα | RXRβ | RXRΓ |
|---|---|---|---|---|---|---|
| 2 | >10³ | >10³ | >10³ | >10³ | >10³ | >10³ |
| 5 | >10³ | >10³ | >10³ | >10³ | >10³ | >10³ |
| 7 | >10³ | >10³ | >10³ | 296 | 302 | 304 |
| 9 | >10³ | >10³ | >10³ | >10³ | >10³ | >10³ |
| 11 | >10³ | >10³ | >10³ | >10³ | >10³ | >10³ |
| 13 | >10⁴ | >10⁴ | >10⁴ | 32 | 57 | 73 |
| 15 | >10³ | >10³ | >10³ | >10³ | >10³ | >10³ |

As it can be seen from the test results summarized in Tables 2, 3 and 4, the therein indicated exemplary compounds of the invention are substantially inactive as RARagonists but are active agonists of all or some of the RXR receptor subtypes.

SPECIFIC EMBODIMENTS

The compounds of this invention can be made by the synthetic chemical pathways illustrated here. The synthetic chemist will readily appreciate that the conditions set out here are specific embodiments which can be generalized to any and all of the compounds represented by Formula 1.

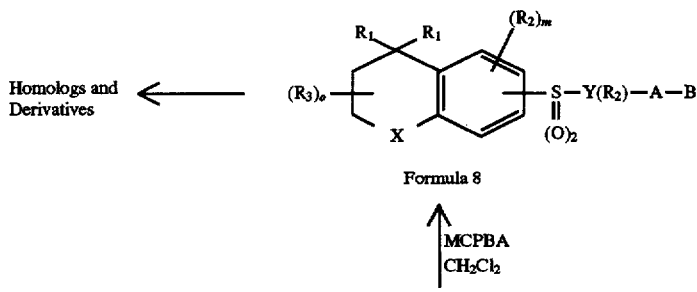

Reaction Scheme 1

-continued
Reaction Scheme 1

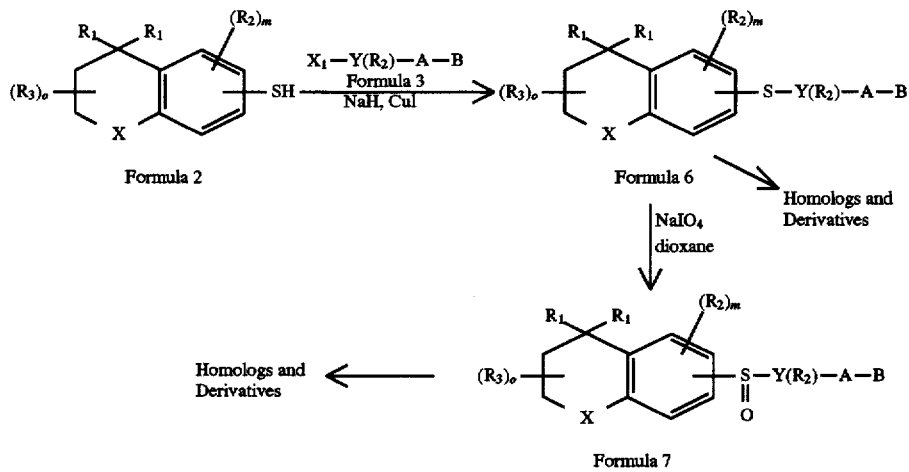

Formula 7

In accordance with Reaction Scheme 1, a condensed cyclic thiol compound of Formula 2 which is appropriately substituted with the $R_1$, $R_2$ and $R_3$ groups (as these are defined in connection with Formula 1) serves as the starting material. The thiol compound of Formula 2 is reacted in the presence of strong base, such as sodium hydride, in a polar aprotic solvent, such as dimethylformamide or hexamethylphosphoramide, and a catalyst, such as copper iodide (CuI), with a reagent of Formula 3 where $X_1$ is halogen and Y, $R_2$, A and B are defined as in connection with Formula 1. The reagent of Formula 3 is, generally speaking, available in accordance with the chemical scientific or patent literature. In the presently preferred compounds of the invention the A group is $(CH_2)_q$ and B is COOH or an ester or amide thereof ($COOR_8$ or $CONR_9R_{10}$) and even more preferably q is zero. The presently preferred reagents in accordance with Formula 3 used for preparation of compounds of the invention have the structure $X_1—Y(R_2)—COOR_8$, and preferred examples are ethyl 4-iodobenzoate (available commercially from Lancaster Chemical Co.), ethyl-2-iodonicotinate and ethyl 2-iodo-5-thiazolecarboxylate. The preparations of ethyl-2-iodonicotinate and of ethyl 2-iodo-5-thiazolecarboxylate are described below in the experimental section.

The thiol reagent of Formula 2 is, generally speaking, also available in accordance with the chemical scientific and patent literature. In one group of preferred compounds of the invention the X group is $[C(R_1)_2]_n$ where n is 1 (tetrahydronaphthalene derivatives) and an example of the starting material for several preferred tetrahydronaphthalene derivatives of the invention is 5,6,7,8-tetrahydro-5,5,8,8-tetramethyl-2-naphthylthiol. The latter compound is available as a result of chlorosulfonylation followed by lithium aluminum hydride reduction of 5,6,7,8-tetrahydro-5,5,8,8-tetramethylnaphthalene in accordance with the procedure of Janssen et al.(BASF A. -G.): Diphenylheteroalkylderivate, ihre Herstellung und daraus hergestellte Arzneimittel und Kosmetika, European Patent Application EP 0 386 452 A1 (Sep. 12, 1990), incorporated herein by reference. The above-mentioned chlorosulfonylation reaction followed by lithium aluminum hydride reduction to provide a thiol compound in the scope of Formula 2 is, generally speaking, applicable for preparing the starting materials (i.e. compounds of Formula 2) for the synthesis of the compounds of the present invention. 5,6,7,8-Tetrahydro-3,5,5,8,8-pentamethyl-2-naphthalene thiol is described in Chemical Abstracts 111:97241 and in French patent FR 2614618 A1, 11-04-1988, incorporated herein by reference. Chroman-6-thiol is described in Chemical Abstracts 101:8709 and in German patent DE 3314467 AI, 01-19-1984, incorporated herein by reference. 2,2-Dimethylchroman-6-thiol is described in Chemical Abstracts 117:48593 and in Japanese patent JP 03232882 A2 10-16-1991, incorporated herein by reference.

In addition to the availability of the thiol compounds of Formula 2 from the foregoing and other scientific publications and patent description (through the above-mentioned chlorosulfonation reaction followed by reduction with $LiAlH_4$) the thiol compounds can also be prepared from bromo substituted tetrahydronaphthalene, chroman, thiochroman and tetrahydroquinoline compounds which are known or available in the art. For example, U.S. Pat. Nos. 5,278,318, 5,348,972, 5,407,937, and 5,407,937 describe 2-alkyl and/or 4-alkyl substituted thiochromans also substituted with a bromo group in the 6 position. U.S. Pat. No. 5,346,585 describes 2-alkyl and/or 4-alkyl substituted thiochromans substituted with a bromo group in the 7 position. U.S. Pat. Nos. 5,324,744, 5,348,975 and 5,346,585 describe 2-alkyl and/or 4-alkyl substituted chromans substituted with a bromo group in the 7 position. U.S. Pat. No. 5,348,972 describes 4-alkyl substituted tetrahydroquinoline compounds substituted with a bromo group in the 6 position. The specifications of U.S. Pat. Nos. 5,278,318, 5,324,744, 5,346,585, 5,348,972, 5,348,975, and 5,407,937 are expressly incorporated herein by reference. These and analogous bromo compounds can be reacted with 2 equivalents of t-butyl lithium in an inert ether-type solvent, and the resulting anion formed after lithium halogen exchange is quenched with sulfur to provide the thiol compounds of Formula 2.

Referring back again to Reaction Scheme 1 the reaction between the thiol compounds of Formula 2 and the aromatic or heteroaromatic halogenated compounds of Formula 3 gives rise to the disubstituted sulfide compounds of Formula 6. The disubstituted sulfide compounds of Formula 6 are within the scope of the present invention and represent a class of preferred compounds of the invention, where with reference to Formula 1, p is zero. The compounds of Formula 6 are oxidized to provide the sulfoxide compounds of Formula 7 which are also within the scope of the invention and where, with reference to Formula 1, p is 1. The oxidation to the sulfoxide stage is conducted with a suitable oxidizing agent, such as sodium periodate ($NaIO_4$) in an ether like solvent, such as dioxane. The disubstituted sulfide compounds of Formula 6 are also oxidized in accordance with Reaction Scheme 1 to the sulfone compounds of Formula S, which are also within the scope of the present invention. In these compounds, with reference to Formula 1, p is 2. Oxidation to the sulfone stage is carried out by reaction with a strong oxidizing agent, such as m-chloroperoxybenzoic acid in an aprotic solvent, preferably methylene chloride. In the situations where the X group of Formula 1 is sulfur (thiochroman derivatives), the above-described oxidation reactions may also oxidize the ring sulfur to the sulfoxide and/or sulfone stage, respectively.

In addition to the above described oxidation reactions the compounds of Formulas 6, 7 and 8 can be subjected to such further transformations, primarily affecting the A–B group, which are per se well known in the art, and which result in still further compounds within the scope of Formula 1. Reactions frequently carried out which affect the B group typically are saponification of an ester group, esterification of a carboxylic acid, formation of an amide or homologation of an acid or ester. These reactions are indicated in Reaction Scheme 1 by conversion to "homologs and derivatives". Regarding these reactions and also regarding the synthesis of halogenated compounds of Formula 3 suitable for the coupling reactions described in Reaction Scheme 1 (where such compound is not available commercially or from a known literature procedure) the following general synthetic methodology is noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and Protecting Groups, Ed. Greene, John Wiley & Sons, 1981.

A means for making compounds where A is $(CH_2)_q$ (q is 1–5) is to subject the compounds of Formula 1, where B is an acid or other function, to homologation, using the well known Arndt-Eistert method of homologation, or other known homologation procedures. Similar homologations (and several of the other herein mentioned synthetic transformations) can be transformed on the reagent $X_1$—Y $(R_2)$—A-B. Compounds of the invention, where A is an alkenyl group having one or more double bonds can be made, for example, by having the requisite number of double bonds incorporated into the reagent $X_1$—Y$(R_2)$— A-B. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-carboxylic acid, ester or like carboxaldehyde. Compounds of the invention where the A group has a triple (acetylenic) bond can be made by using the corresponding aryl or heteroaryl aldehyde intermediate. Such intermediate can be obtained by reactions well known in the art, for example, by reaction of a corresponding methyl ketone with strong base, such as lithium diisopropylamide.

The acids and salts derived from compounds of Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium or lithium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979.), or dimethyl sulfoxide/oxalyl chloride in methylene chloride (Omura, K., Swern, D., Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 1 where B is H can be prepared from the corresponding halogenated aromatic compounds, preferably where the halogen is I.

Specific Examples

6-Iodonicotinic acid

To 27.97 g (186.6 mmol) of sodium iodide cooled to –78° C. was added 121.77 g (71.6 ml, 952.0 mmol) of hydroiodic acid (57 wt %). The reaction mixture was allowed to warm slightly with stirring for 5 minutes, and then 30.00 g (190.4 mmol) of 6-chloronicotinic acid was added. The resulting mixture was allowed to warm to room temperature with stirring and then heated at 120°–125° C. in an oil bath for 42 hours. A dark brown layer formed above the yellow solid material. The reaction mixture was allowed to cool to room temperature and then poured into acetone (chilled to 0° C.). The resultant yellow solid was collected by filtration, washed with 200 ml of 1N $NaHSO_3$ solution, and dried in high vacuum (3 mmHg) to give the title compound as a pale yellow solid.

PMR (DMSO-$D_6$): δ 7.90 (1H, dd, J=8.1, 2 Hz), 7.99 (1H, d, J=8.1 Hz), 8.80 (1H, d, J=2.Hz).

Ethyl 6-iodonicotinate

To a suspension of 23.38 g (94.2 mmol) of 6-iodonicotinic acid in 100 ml of dichloromethane was added a solution of 19.86 g (103.6 mmol) of 1-(3-dimethylaminopropyl)-3-ethylcarbodiimide hydrochloride in 250 ml of dichloromethane. To this suspension was added 12.40 g (15.8 ml, 269.3 mmol) of ethanol (95%) and 1.15 g (9.4 mmol) of 4-dimethylaminopyridine. The resulting solution mixture was then heated at 50° C. in an oil bath for 24.5 hours, concentrated in vacuo, partitioned between 200 ml of water and 250 ml of ethyl ether, and the layers were separated. The aqueous phase was washed with 2×150 ml-portions of ethyl ether. All organic phases were combined, washed once with 75 ml of brine solution, dried over $MgSO_4$, filtered and concentrated in vacuo to a yellow solid. Purification by flash chromatography (silica, 10% ethyl acetate in hexane) yielded the title compound as a white solid.

PMR ($CDCl_3$): δ 1.41 (3H, t, J=7.1 Hz), 4.41 (2H, q, J=7.1 Hz), 7.85 (1H, d, J=8.2 Hz), 7.91 (1H, dd, J=8.2, 2.1 Hz), 8.94 (1H, d, J=2.1 Hz).

Ethyl 2-iodo-5-thiazolecarboxylate

To a solution of 4.96 g (31.5 mmol) of 2-trimethylsilylthiazole in 100 ml of ether stirring at −78 ° C. under argon, was dropwise added n-BuLi (23.0 mL, 36.8 mmol, 1.6 M in hexanes) and the resulting mixture stirred at −78 ° C. for 30 min. Ethyl chloroformate (7.60 mL, 10.6 g, 98 mmol) was added and the reaction stirred at −78 ° C. for 30 min and at room temperature for 30 min. The solution was then recooled to −78° C. where a solution of 10.75 g (42.5 mmol) of 12 in 50 mL of tetrahydrofuran was cannulated into the cool solution. The reaction was warmed slowly to room temperature and stirred for 15 h. The reaction was then cooled to −78° C., quenched with water and sodium thiosulfate, and extracted with diethyl ether (3×). The organic layers were combined, washed with brine, dried ($Na_2SO_4$), filtered, and the solvents removed in-vacuo. The crude product was purified by flash chromatography on silica gel (85:15/hexane:ethyl acetate) to give the title compound as an oil (0.89 g, 10%): PNMR (300 MHz, $CDCl_3$) δ 1.38 (t, 3H, J=7.1 Hz), 4.36 (q, 2H, J=7.1 Hz), 8.11 (s, 1H).

Ethyl 4-(5,6,7,8-tetrahydro-5,5,8,8-tetramethyl-2-naphthylthio)benzoate (Compound 1)

Sodium hydride (0.807 g, 60% dispersion in Oil, 21 mmol) was rinsed 3× with hexane and dried under vacuum. The vacuum was broken with dry argon and to this was added 10.0 mL of dimethylformamide and the mixture cooled to 0° C. 5,6,7,8-Tetrahydro-5,5,8,8-tetramethyl-2-naphthylthiol available in accordance with Janssen et al. European Patent Application EP 0 386 452 A1, Sep. 12, 1990, (702 mg, 3.2 mmol) was then added and the resulting mixture stirred at 0°–10° C. for 1.25 h. Copper (I) iodide (0.592 g, 3.1 mmol) was added, the mixture stirred at 0° C. for 45 min and a solution of ethyl 4-iodobenzoate (0.839 g, 3.04 mmol) in 2.0 ml of dimethylformamide was added. The mixture was heated to 75° C. for 48 h, the bath removed, and stirred at room temperature for 48 h. The reaction was then poured onto ice and extracted with ether (4×), the organic layers were combined, washed with brine, dried ($MgSO_4$), filtered, and the solvents removed in-vacuo to give an orange solid. The crude product Has purified by flash chromatography on silica gel (98:2/hexane:ethyl acetate) to give the title compound as a clear oil (0.32 g, 27%):

PNMR (300 MHz, $CDCl_3$) δ 1.26 (s, 6H), 1.30 (s, 6H), 1.37 (t, 3H, J=7.1 Hz), 1.70 (s, 4H), 4.34 (q, 2H, J=7.1 Hz), 7.17 (d, 2H J=8.5 Hz), 7.22 (dd, 1H, J=2.0, 8.2 Hz), 7.32 (d, 1H, J=8.2 Hz), 7.44 (d, 1H, J=2.0 Hz), 7.89 (d, 2H J=8.5 Hz).

4-(5,6,7,8-Tetrahydro-5,5,8,8-tetramethylnaphthylthio)benzoic acid (Compound 2)

To a solution of 70 mg (0.19 mmol) of ethyl 4-(5,6,7,8-tetrahydro-5,5,8,8-tetramethylnaphthylthio)benzoate (Compound 1) in 4.0 mL of tetrahydrofuran was added 1.0 mL of LiOH (1.9N aqueous solution) and 1.5 mL of MeOH. The solution was heated at 55° C. for 3 h, cooled to room temperature and concentrated in vacuo. The residue was diluted with water and extracted with hexane. The aqueous layer was acidified to pH=1 using 10% HCl and extracted twice with diethyl ether. The combined organic layers were washed with brine, dried ($MgSO_4$), filtered and the solvents removed in vacuo. Purification of crude product by flash chromatography on silica gel (7:3/hexane:ethyl acetate) gave the title compound as a white solid (40 rag, 62%):

PNMR (300 MHz, $CDCl_3$) δ 1.27 (s, 6H), 1.31 (s, 6H), 1.71 (s, 4H), 7.18 (d, 2H J=8.6 Hz), 7.25 (dd, 1H, J=2.0, 8.2 Hz), 7.34 (d, 1H, J=8.2 Hz), 7.47 (d, 1H, J=2.0 Hz), 7.95 (d, 2H J=8.6 Hz).

Ethyl 4-(5,6,7,8 -tetrahydro-5,5,8,8-tetramethyl-2-naphthylsulfoxy)benzoate (Compound 3)

To a solution of ethyl 4-(5,6,7,8-tetrahydro-5,5,8,8-tetramethyl-2-naphthylthio)benzoate (Compound 1, 0.18 g, 0.31 mmol) in 4 ml of dioxane was dropwise added a solution of sodium periodate (0.181 g, 0.85 mmol) in 1.7 mL $H_2O$ and 4.0 mL of MeOH. The resulting mixture was stirred at 50° C. for 120 h. The reaction was then cooled to room temperature, brine was added and the mixture extracted using ether (2×). The combined organic layers were then dried ($MgSO_4$), filtered and concentrated to give a clear oil. Purification by flash chromatography (85:15/hexane: ethyl acetate) gave the title compound as a clear oil (57 mg, 30%):

PNMR (300 MHz, $CDCl_3$) δ 1.24 (s, 6H), 1.26 (s, 3H), 1.28 (s, 3H), 1.39 (t, 3H, J=7.1 Hz), 1.67 (s, 4H), 4.38 (q, 2H, J=7.1 Hz), 7.27 (dd, 1H, J=1.9, 8.3 Hz), 7.36 (d, 1H J=8.3 Hz), 7.64 (d, 1H, J=1.9 Hz), 7.72 (d, 2H, J=8.4 Hz), 8.14 (d, 2H J=8.4 Hz).

Ethyl 2-(5,6,7,8-tetrahydro-5,5,8,8-tetramethyl-2-naphthylsulfonyl)benzoate (Compound 4 )

To a solution of 230 mg (0.63 mmol) of ethyl 4-(5,6,7,8-tetrahydro-5,5,8,8-tetramethyl-2-naphthylthio)benzoate (Compound 1) in 5.0 mL of methylene chloride was added m-chloroperoxybenzoic acid (200 mg, 0.60 mmol, 50–60%) and the resulting solution stirred at room temperature for 24 h. The reaction mixture was diluted with water and extracted with methylene chloride (2×). The combined organic layers were dried ($MgSO_4$), filtered, and the solvents were removed in vacuo to give a white solid. The crude product was purified by flash chromatography on silica gel (96:4/hexane:ethyl acetate) to give the title compound as a white solid (0.11 g, 87%): PNMR (300 MHz, $CDCl_3$) δ 1.25 (s, 6H), 1.29 (s, 6H), 1.39 (t, 3H, J=7.1 Hz), 1.68 (s, 4H), 4.39 (q, 2H, J=7.1 Hz), 7.42 (d, 2H J=8.4 Hz), 7.61 (dd, 1H, J=2.1, 8.4 Hz), 7.90 (d, 1H, J=2.1 Hz), 8.00 (d, 2H J=8.5 Hz), 8.15 (d, 2H J=8.5 Hz).

4-(5,6,7,8-tetrahydro-5,5,8,8-tetramethyl-2-naphthylsulfonyl)benzoic acid (Compound 5)

To a solution of 95 mg (0.23 mmol) of ethyl 4-(5,6,7,8-tetrahydro-5,5,8,8-tetramethyl-2-naphthylsulfonyl)benzoate (Compound 4) in 4.0 mL of tetrahydrofuran was added 1.0 mL of LiOH (2.6N aqueous solution) and 1.4 mL of MeOH. The solution was heated at 55° C. for 2.5 h, cooled to room temperature and concentrated in vacuo. The residue was diluted with brine, acidified to pH=1 using 10% HCl and extracted with ether (2×). The combined organic layers were washed with brine, dried (MgSO₄), filtered and the solvents were removed in vacuo to give the title compound as a white solid (80 mg, 91%):

PNMR (300 MHz, CDCl₃) δ 1.26 (s, 6H), 1.29 (s, 6H), 1.68 (s, 4H), 7.17 (d, 2H J=8.5 Hz), 7.42 (d, 1H, J=8.4 Hz), 7.63 (dd, 1H, J=2.1, 8.4 Hz), 7.92 (d, 1H, J=2.1 Hz), 8.04 (d, 2H J=8.5 Hz), 8.22 (d, 2H J=8.5 HZ).

Ethyl 4-(5,6,7,8-tetrahydro-3,5,5,8,8-pentamethyl-2-naphthylthio)benzoate (Compound 6)

Sodium hydride (65 mg, 60% dispersion in oil, 1.62 mmol) was rinsed 3× with hexane and dried under vacuum. The vacuum was broken with dry argon and 2.5 mL of hexamethylphosphoramide (HMPA) and 5,6,7,8-tetrahydro-3,5,5,8,8-pentamethyl-2-naphthylthiol (see Janssen et al. European Patent Application EP 0 386 452 Al) (0.38 g, 1.62 mmol) were added sequentially. After 30 min at 50° C., copper (I) iodide (257 mg, 1.35 mmol) was added, which caused the solution to become deep green. The solution was stirred for 15 min and ethyl 4-iodobenzoate (373 mg, 1.35 mmol) was added. The solution was heated to 90° C. for 5 h, the bath removed, and stirring continued overnight at room temperature. Water was added and the products extracted with diethyl ether (3×). The combined ether layers were washed with brine, dried (MgSO₄), filtered and the solvents removed in vacuo. The residue was purified by flash chromatography on silica gel (95:5/hexane:ethyl acetate) to give the title compound as a light yellow solid (260 mg, 50%):

PNMR (300 MHz, CDCl₃): δ 1.24 (s, 6H), 1.30 (s, 6H), 1.36 (t, 3H, J=7.1 Hz), 1.69 (s, 4H), 2.28 (s, 3H), 4.33 (q, 2H, J=7.1 Hz), 7.05 (d, 2H, J=8.6 Hz), 7.23 (s, 1H), 7.26 (s, 1H), 8.87 (d, 2H, J=8.6 Hz)

4-(5,6,7,8-tetrahydro-3,5,5,8,8-pentamethyl-2-Daphthylthio)benzoic acid (Compound 7)

Ethyl 4-(5,6,7,8-tetrahydro-3,5,5,8,8-pentamethyl-2-naphthylthio)benzoate (Compound 6, 170 mg, 0.44 mmol) was dissolved in ethyl alcohol (4 mL) and the solution treated with 2N aqueous KOH (2 mL). The solution was heated to 50° C. for 4 h and concentrated in vacuo. The residue was treated with diethyl ether, cooled to 0° C., and acidified with 10% aqueous HCl. The product was extracted with diethyl ether, washed with water, brine, dried (MgSO₄), filtered and the solvents were removed under reduced pressure to give the title compound as a yellow solid (158 mg, 100%):

PNMR (300 MHz, CDCl₃): δ 1.25 (s, 6H), 1.31 (s, 6H), 1.69 (s, 4H), 2.29 (s, 3H), 7.05 (d, 2H, J=8.5 Hz), 7.25 (s, 1H), 7.26 (s, 1H), 7.92 (d, 2H, J=8.5 Hz)

Ethyl 4-(5,6,7,8-tetrahydro-3,5,5,8,8-pentamethyl-2-naphthylsulfoxy)benzoate (Compound 8)

To a solution of ethyl 4-(5,6,7,8-tetrahydro-3,5,5,8,8-pentamethyl-2-naphthylthio)benzoate (Compound 6, 0.12 g, 0.31 mmol) in 4 ml of dioxane was dropwise added 1.0 mL of 0.42M sodium periodate (0.42 mmol, 180 mg in 1.3 mL H₂O and 0.7 mL of MeOH). An additional 6.0 ml of methanol was added and the resulting mixture was stirred at room temperature for 42 h. The reaction was then heated at 50° C. for 200 h. Additional sodium periodate (80 mg, 0.38 mmol) and 2.0 mL of dioxane was added during this time. The reaction was then cooled to room temperature, brine was added and the mixture extracted using ether (2×). The organic layers were then dried (MgSO₄), filtered and concentrated to give a clear oil. Purification by flash chromatography (85:15/hexane:ethyl acetate) gave the title compound as a clear oil (65 mg, 52%):

PNMR (300 MHz, CDCl₃) δ 1.23 (s, 3H), 1.24 (s, 3H), 1.26 (s, 3H), 1.30 (s, 3H), 1.39 (t, 3H, J=7.1 Hz), 1.67 (s, 4H), 2.31 (s, 3H), 4.38 (q, 2H, J=7.1 Hz), 7.08 (s, 1H), 7.66 (d, 2H J=8.4 Hz), 7.76 (s, 1H), 8.12 (d, 2H J=8.4 Hz).

4-(5,6,7,8-tetrahydro-3,5,5,8,8-pentamethyl-2-naphthylsulfoxy)benzoic acid (Compound 9)

To a solution of 58 mg (0.15 mmol) of ethyl 4-(5,6,7,8-tetrahydro-3,5,5,8,8-pentamethyl-2-naphthylsulfoxy)benzoate (Compound 8) in 4.0 mL of tetrahydrofuran was added 1.0 mL of LiOH (2N aqueous solution) and 2.0 ml of MeOH. The solution was heated at 55° C. for 2 h and stirred at room temperature for 8 h. The reaction mixture was then concentrated in vacuo. The residue was diluted with brine and 10% HCl and extracted with diethyl ether (2×). The combined ether layers were dried (MgSO₄), filtered, and the solvents removed in vacuo to give the title compound as a white solid (0.39 mg, 72%):

PNMR (300 MHz, CDCl₃) δ 1.22 (s, 3H), 1.24 (s, 3H), 1.26 (s, 3H), 1.29 (s, 3H), 1.66 (s, 4H), 2.34 (s, 3H), 7.10 (s, 1H), 7.70 (d, 2H J=8.3 Hz), 7.76 (s, 1H), 8.17 (d, 2H, J=8.3 Hz).

Ethyl 4-(5,6,7,8-tetrahydro-3,5,5,8,8-pentamethyl-2-naphthylsulfonyl)benzoate (Compound 10)

To a solution of 69 mg (0.18 mmol) of ethyl 4-(5,6,7,8-tetrahydro-3,5,5,8,8-pentamethyl-2-naphthylthio)benzoate (Compound 6) in 2.0 mL of methylene chloride was dropwise added a solution of 87 mg of m-chloroperoxybenzoic acid (0.27 mmol, 50–60%) in 2.0 mL of methylene chloride, and the resulting solution was stirred for 3 h. The reaction was diluted with water and extracted with methylene chloride (2×). The combined organic layers were dried (MgSO₄), filtered, and the solvents removed in vacuo to give a white solid. The crude product was purified by flash chromatography on silica gel (9:l/hexane:ethyl acetate) to give the title compound as a white solid (51 mg, 94%):

PNMR (300 MHz, CDCl₃) δ 1.25 (s, 6H), 1.34 (s, 6H), 1.39 (t, 3H, J=7.1 Hz), 1.70 (s, 4H), 2.33 (s, 3H), 4.40 (q, 2H, J=7.1 Hz), 7.11 (s, 1H), 7.90 (d, 2H J=8.5 Hz), 8.15 (s & d overlapping, 3H).

4-(5,6,7,8-tetrahydro-3,5,5,8,8-pentamethyl-2-naphthylsulfonyl)benzoic acid (Compound 11)

To a solution of 50 mg (0.12 mmol) of ethyl 4-(5,6,7,8-tetrahydro-3,5,5,8,8-pentamethyl-2-naphthylsulfonyl)benzoate (Compound 10) in 3.0 mL of tetrahydrofuran was added 1.0 mL of LiOH (1N aqueous solution). The solution was heated at 50° C. for 3 h, cooled to room temperature and concentrated in vacuo. The residue was diluted with brine, acidified using 10% HCl and extracted with ether (2×). The combined ether layers were dried (MgSO₄), filtered, and the solvents were removed in vacuo to give the title compound as a white solid (45 mg, 98%):

PNMR (300 MHz, CDCl₃) δ 1.25 (s, 6H), 1.34 (s, 6H), 1.70 (s, 4H), 2.33 (s, 3H), 7.12 (s, 1H), 7.95 (d, 2H J=8.4 Hz), 8.15 (s, 1H), 8.22 (d, 2H, J=8.4 Hz).

Ethyl 2-(5,6,7,8-tetrahydro-3,5,5,8,8-pentamethyl-2-naphthylthio)nicotinate (Compound 12)

Sodium hydride (171 mg, 60% dispersion in oil, 4.3 mmol) was rinsed 3× with hexane and dried under vacuum.

The vacuum was broken with dry argon and 6.6 mL of hexamethylphosphoramide (HMPA) and 5,6,7,8-tetrahydro-3,5,5,8,8-pentamethyl-2-naphthylthiol (1.0 g, 4.27 mmol) were added sequentially. After 30 min at 50° C., copper (I) iodide (678 mg, 3.56 mmol) was added, which caused the solution to become deep green. The solution was stirred for 15 min and ethyl 2-iodonicotinate (986 mg, 3.56 mmol) was added. The solution was heated to 90° C. for 5 h, the bath was removed, and stirring was continued overnight at room temperature. Water was added and the products were extracted with diethyl ether (3×). The combined ether layers were washed with brine, dried (MgSO$_4$), filtered and the solvents removed in vacuo. The residue was purified by flash chromatography on silica gel (95:5/hexane:ethyl acetate) to give the title compound as a light yellow solid (642 mg, 47%):

PNMR (300 MHz, CDCl$_3$): δ 1.26 (s, 6H), 1.31 (s, 6H), 1.37 (t, 3H, J=7.1 Hz), 1.69 (s, 4H), 2.32 (s, 3H), 4.36 (q, 2H, J=7.1 Hz), 6.68 (d, 1H, J=8.0 Hz), 7.73 (s, 1H), 7.53 (s, 1H), 7.99 (dd, 1H, J=2.3, 8.0 Hz), 9.00 (d, 1H, J=2.3 Hz)

2-(5,6,7,8-Tetrahydro-3,5,5,8,8-pentamethyl-2-naphthylthio)nicotinic acid (Compound 13)

To a solution of ethyl 2 - ( 5,6,7,8-tetrahydro-3,5,5,8,8-pentamethyl-2-naphthylthio)nicotinate (Compound 12, 300 mg, 0.78mmol) and ethanol (8 mL) was added 2N KOH (2 mL) and the resulting solution stirred at 50° C. for 34 h. The solution was concentrated in vacuo, water added, and the mixture was acidified with 10% aqueous HCl. The product was extracted with methylene chloride (3×) and the combined organic extracts were washed with brine, dried (MgSO$_4$), filtered and concentrated in vacuo. The solid residue was recrystalized from acetonitrile/methanol (4:1) to give the title compound (233 mg, 84%) as light yellow crystals:

PNMR (300 MHz, CDCl$_3$) δ 1.21 (s, 6H), 1.26 (s, 6H), 1.63 (s, 4H), 2.23 (s, 3H), 6.81 (d, 1H, J=8.2 Hz), 7.39 (s, 1H), 7.50 (s, 1H), 7.05 (dd, 1H, J=2.1, 8.2 Hz), 8.84 (d, 1H, J=2.1 Hz)

Ethyl 2-(5,6,7,8-tetrahydro-3,5,5,8,8-pentamethyl-2-naphthylthio)-5-thiazolecarboxylate (Compound 14)

Sodium hydride (0.057 g, 60% dispersion in oil, 2.4 mmol) was rinsed 3× with hexane and dried under vacuum. The vacuum was broken and dry argon was added. To this was added 5.0 mL of hexamethylphosphoramide. 5,6,7,8-tetrahydro-3,5,5,8,8-pentamethyl-2-naphthylthiol (445 mg, 1.9 mmol) was then added and the resulting mixture heated at 50° C. for 45 min. Copper (I) iodide (0.36 g, 1.9 mmol) was added and the mixture heated at 55° C. for 1.5 h and a solution of ethyl 2-iodo-5-thiazolecarboxylate (0.65 g, 2.3 mmol) in 2.0 ml of hexamethylphosphoramide was added. The mixture was heated to 95° C. for 2 h. The reaction was then cooled to 0° C., quenched with water, and extracted with diethyl ether (2×). The organic layers were combined, washed with brine, dried (MgSO$_4$), filtered, and the solvents were removed in vacuo. The crude product was purified by flash chromatography on silica gel (85:15/hexane:ethyl acetate) to give the title compound as an orange oil (0.30 g, 41%)

PNMR (300 MHz, CDCl$_3$) δ 1.28 (s, 6H), 1.32 (s, 6H), 1.32 (t, 3H, J=7.1 Hz), 1.70 (s, 4H), 2.41 (s, 3H), 4.29 (q, 2H, J=7.1 Hz), 7.30 (s, 1H ), 7.60 (s, 1H), 8.19 (s, 1H).

2-(5,6,7,8-Tetrahydro-3,5,5,8,8-pentamethyl-2-naphthylthio)-5-thiazolecarboxylic acid (Compound 15)

To a solution of 0.183 g (0.47 mmol) of ethyl 2-(5,6,7,8-tetrahydro-3,5,5,8,8-pentamethyl-2-naphthylthio)-5-thiazolecarboxylate (Compound 14) in 2.0 mL of THF was added 1.0 mL of LiOH (2.1N aqueous solution) and 1.0 mL of MeOH. The solution was heated at 50° C. for 1 h, cooled to room temperature and concentrated in vacuo. The residue was diluted with water, the aqueous layer acidified to pH=1 using 10% HCl and extracted with ether. The combined organic layers were washed with brine, dried (MgSO$_4$), filtered, and the solvents removed in vacuo to give the title compound as a white solid (131 mg, 78%): PNMR (300 MHz, CD$_3$OD) δ 1.28 (s, 6H), 1.32 (s, 6H), 1.73 (s, 4H), 2.40 (s, 3H), 7.42 (s, 1H), 7.63 (s, 1H), 8.12 (s, 1H).

What is claimed is:

1. A compound of the formula

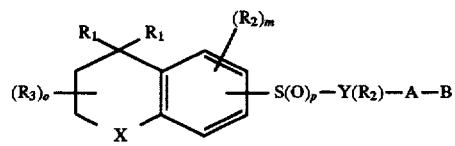

wherein

X is n where n is an integer between 0 and 2;

R$_1$ is independently H or alkyl of 1 to 6 carbons;

R$_2$ is hydrogen, lower alkyl of 1 to 6 carbons, F, Cl, Br, I, fluoro substituted alkyl of 1 to 6 carbons, OH, SH, alkoxy of 1 to 6 carbons, or alkylthio of 1 to 6 carbons;

R$_3$ is hydrogen, lower alkyl of 1 to 6 carbons or F;

m is an integer having the value of 0–3;

o is an integer having the value of 0–4;

p is an integer having the value of 0–2;

Y is heteroaryl selected from a group consisting of pyridazinyl, pyrimidinyl, pyrazinyl, thiazolyl, oxazolyl, imidazolyl and pyrrazolyl, said heteroaryl groups being optionally substituted with one or two R$_2$ groups;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, COOR$_8$, CONR$_9$R$_{10}$, —CH$_2$OH, CH$_2$OR$_{11}$, CH$_3$OCOR$_{11}$, CHO, CH(OR$_{12}$)$_2$, CHOR$_{13}$O, —COR$_7$, CRT(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or (trimethylsilyl)alkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

2. A compound in accordance with claim 1 wherein and n is 1.

3. A compound in accordance with claim 1 wherein Y is thiazolyl.

4. A compound of the formula

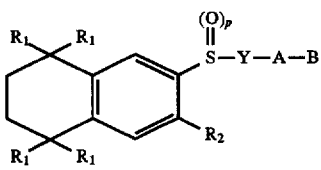

wherein $R_1$ is independently H or alkyl of 1 to 6 carbons;
$R_2$ is hydrogen, lower alkyl of 1 to 6 carbons, F, or fluoro substituted alkyl of 1 to 6 carbons;
Y is thiazolyl;
p is an integer having the value of 0–2;
A is $(CH_2)_q$ where q is 0–5, lower branched chain alkyl having 3–6 carbons, cycloalkyl having 3–6 carbons, and
B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-CORT$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_s$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_n$ is lower alkyl, phenyl or lower alkylphenyl, $R_{12}$ is lower alkyl, and $R_{13}$ is divalent alkyl radical of 2–5 carbons.

5. A compound in accordance with claim 4 wherein the $R_1$ groups are methyl.

6. A compound in accordance with claim 5 wherein $R_2$ is H or $CH_3$.

7. A compound in accordance with claim 6 wherein A is $(CH_2)_q$ where q is 0 and wherein B is COOH or a pharmaceutically acceptable salt thereof, $COOR_8$, or $CONR_9R_{10}$.

8. A compound in accordance with claim 7 wherein Y is 2-thiazolyl substituted in the 5 position with the A–B group.

9. A compound in accordance with claim 8 wherein p is zero.

10. A compound in accordance with claim 9 which is ethyl 2-(5,6,7,8-tetrahydro-3,5,5,8,8-pentamethyl-2-naphthylthio)-5-thiazolecarboxylate and 2-(5,6,7,8-tetrahydro-3,5,5,8,8-pentamethyl-2-naphthylthio)-5-thiazolecarboxylic acid.

* * * * *

UNITED STATES PATENT AND TRADEMARK OFFICE
CERTIFICATE OF CORRECTION

PATENT NO. : 5,672,710　　　　　　　　　　Page 1 of 3
DATED : September 30, 1997
INVENTOR(S) : Beard et al.

It is certified that error appears in the above-indentified patent and that said Letters Patent is hereby corrected as shown below:

Column 1, line 14, "tetrahydronapthalenyl" should be --tetrahydronaphthalenyl--.

Column 2, line 11, delete "5,130,335 (Chandraratna et al.),".

Column 2, line 21, after "Med", add --.--.

Column 2, line 45, after "receptors", add --are--.

Column 5, line 48, after "may", delete "by".

Column 7, line 49, "it" should be --its--.

Column 12, line 35, "chlorosulfonation" should be --chlorosulfonylation--.

Column 15, line 65, after "7.17 (d, 2H", add --,--.

Column 15, line 66, after "7.89 (d, 2H", add --,--.

Column 16, line 17, after "7.18 (d, 2H", add --,--.

Column 16, line 19, after "2H", add --,--.

Column 16, line 37, after "7.36 (d, 1H", add --,--.

Column 16, line 39, after "2H", add --,--.

Column 16, line 57, after "7.42 (d,2H", add --,--.

Column 16, line 58, after "8.00 (d, 2H", add --,--.

Column 16, line 59, after "8.15 (d,2H", add --,--.

Column 17, line 8, after "7.17 (d, 2H", add --,--.

Column 17, line 10, after the first occurrence of "2H", add --,--.

Column 17, line 10, after "8.22 (d, 2H", add --,--.

UNITED STATES PATENT AND TRADEMARK OFFICE
CERTIFICATE OF CORRECTION

PATENT NO. : 5,672,710
DATED : September 30, 1997
INVENTOR(S) : Beard et al.

Page 2 of 3

It is certified that error appears in the above-indentified patent and that said Letters Patent is hereby corrected as shown below:

Column 2, line 7, "U.S. Pat. Nos." should begin a new paragraph.

Column 2, line 23, "54" should be --354--.

Column 3, line 2, after "Formula", add --1--.

Column 5, line 1, "Formula I" should be --Formula 1--.

Column 7, line 19, "ache" should be --acne--.

Column 8, line 1, "Assay of Retinoid-like Biological Activity" should be a new heading.

Column 8, line 28, "RXR and RXR" should be --RXR and RXR--.

Column 8, line 40, "WO W093/11755" should be --W093/11755--.

Column 8, line 49, "PAR" should be --RAR--.

Column 8, line 54, "RXRexpression" should be --RXR expression--.

Column 10, lines 26-27, "RARagonists" should be --RAR agonists--.

Column 13, line 7, "Formula S" should be --Formula 8--.

Column 14, line 62, "(DMSO $D_6$)" should be --(DMSO $d_6$)--.

Column 15, line 15, "6" should be -- --.

Column 15, line 29, "12" should be --$I_2$--.

Column 15, line 43, "0,807" should be --0.807--.

Column 15, line 43, "Oil" should be --oil--.

Column 15, line 52, "0,592" should be --0.592--.

Column 15, line 53, "0,839" should be --0.839--.

UNITED STATES PATENT AND TRADEMARK OFFICE
CERTIFICATE OF CORRECTION

PATENT NO. : 5,672,710
DATED : September 30, 1997
INVENTOR(S) : Beard et al.

It is certified that error appears in the above-indentified patent and that said Letters Patent is hereby corrected as shown below:

Column 15, line 60, "Has" should be --was--.
Column 16, line 15, "rag" should be --mg--.
Column 17, line 40, "Daphthylthio" should be --naphthylthio--.
Column 20, line 52, "$CRT(OR_{12})_2$" should be --$CR_7(OR_{12})_2$--.
Column 21, line 22, "-CORT" should be -- -$COR_7$--.
Column 21, line 24, "$R_s$" should be --$R_8$--.
Column 22, line 4, "$R_n$" should be --$R_{11}$--.
Column 18, line 10, after "8.12 (d, 2H", add --,--.
Column 18, line 26, after "7.70 (d, 2H", add --,--.
Column 18, line 46, after "7.90 (d, 2H", add --,--.
Column 18, line 61, after "7.95 (d, 2H", add --,--.
Column 19, line 31, "recrystalized" should be --recrystallized--.
Column 20, line 64, delete "and".

Signed and Sealed this

Twenty-fourth Day of March, 1998

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,672,710
DATED : September 30, 1997
INVENTOR(S) : Beard et al.

It is certified that error appears in the above-identified patent and that said Letters Patent is hereby corrected as shown below:

Column 20, line 27, the first occurrence of "n" should be --$[C(R_1)_2]_n$--.

Signed and Sealed this

First Day of September, 1998

BRUCE LEHMAN

Attest:

Attesting Officer

Commissioner of Patents and Trademarks